(12) United States Patent
Yamashita et al.

(10) Patent No.: US 7,189,315 B2
(45) Date of Patent: Mar. 13, 2007

(54) ION SENSOR AND CLINICAL ANALYZER USING THE SAME

(75) Inventors: Kotaro Yamashita, Mito (JP); Koichi Tayama, Hitachinaka (JP); Noriko Yoshioka, Hitachinaka (JP); Yasuhisa Shibata, Naka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 601 days.

(21) Appl. No.: 10/246,458

(22) Filed: Sep. 19, 2002

(65) Prior Publication Data

US 2003/0152486 A1    Aug. 14, 2003

(30) Foreign Application Priority Data

Nov. 12, 2000   (JP)   ............... 2002-004035

(51) Int. Cl.
  C12Q 1/68    (2006.01)
  G01N 27/26   (2006.01)
  G01N 15/06   (2006.01)
  G01N 33/00   (2006.01)
  G01N 33/48   (2006.01)

(52) U.S. Cl. .............. 204/416; 422/50; 422/68.1; 422/82.01; 422/82.02; 422/82.03; 73/1.01; 73/1.02; 436/43; 436/149; 436/151; 204/414; 204/415; 204/417; 204/418; 204/419; 204/420; 204/421; 204/422

(58) Field of Classification Search ............ 422/50, 422/68.1, 82.01, 82.02, 82.03; 73/1.01, 1.02, 73/53.01; 436/43, 149, 151; 204/414, 415, 204/416, 417, 418, 419, 420, 421, 422

See application file for complete search history.

(56) References Cited

U.S. PATENT DOCUMENTS

| | | | | |
|---|---|---|---|---|
| 4,040,928 A | * | 8/1977 | Kraus et al. ................. | 204/419 |
| 4,627,893 A | * | 12/1986 | Cormier et al. ............. | 205/779 |
| 4,713,165 A | * | 12/1987 | Conover et al. ........ | 204/403.05 |
| 4,758,325 A | * | 7/1988 | Kanno et al. ................. | 204/411 |
| 4,839,020 A | * | 6/1989 | Yamaguchi et al. ......... | 204/431 |
| 4,891,125 A | * | 1/1990 | Schultz ........................ | 204/435 |
| 4,913,793 A | * | 4/1990 | Leonard ...................... | 204/433 |
| 4,935,117 A | * | 6/1990 | Uematsu et al. ............. | 204/411 |
| 5,182,004 A | * | 1/1993 | Kohno .................... | 204/403.05 |
| 5,413,685 A | * | 5/1995 | Ozawa et al. ................ | 204/416 |
| 5,417,836 A | * | 5/1995 | Masuda et al. .............. | 204/419 |
| 5,472,590 A | * | 12/1995 | Yamashita et al. ........... | 257/253 |
| 5,505,836 A | * | 4/1996 | Miyahara et al. ............ | 204/418 |
| 5,567,302 A | * | 10/1996 | Song et al. ............... | 205/777.5 |
| 5,580,441 A | * | 12/1996 | Amemiya et al. ........... | 205/789 |
| 5,700,360 A | * | 12/1997 | Chan et al. ................... | 205/778 |
| 6,197,172 B1 | * | 3/2001 | Dicks et al. .................. | 204/416 |
| 6,398,931 B1 | * | 6/2002 | Burchette et al. ............ | 204/416 |

* cited by examiner

*Primary Examiner*—Brian Sines
(74) *Attorney, Agent, or Firm*—Mattingly, Stanger, Malur & Brundidge, P.C.

(57) ABSTRACT

An ion sensor has a flow path through which a sample flows. An ion-exchange membrane is in contact with the sample in the sample flow path. An internal solution is provided on one side of the ion-exchange membrane. An internal electrode is provided so as to come in contact with the internal solution. The surface of the ion-exchange membrane that does not come in contact with the sample is coated with a two-liquid-mixed epoxy resin.

6 Claims, 4 Drawing Sheets

ION SENSOR AND CLINICAL ANALYZER USING THE SAME

BACKGROUND OF THE INVENTION

1. Field of the Invention

This invention relates to an ion sensor suited for the analysis of ions in a biological fluid/material. More specifically, the invention relates to an ion sensor suited for the analysis for potentiometrically measuring ions and to a clinical analyzer.

2. Description of Related Art

Ion sensors have a feature of selectively determining a particular ion concentration in the solution and have heretofore been used in a wide field of applications such as monitoring the concentration of particular ions and analyzing the water. In the field of medical treatment, in particular, the ion sensors have been used for determining ions contained in the biological fluid/material such as blood and urine, e.g., for determining chloride ions and potassium ions. This is based on that the concentration of particular ions in the biological fluid/material has an intimate relationship to the metabolic reaction of the biological fluid/material. Upon measuring the ion concentrations, various diseases such as hypertension, kidney disorder, nervous disorder and the like diseases can be diagnosed. Between the ionic activity a treated by the ion sensor and the potential E exhibited by the ion sensor, there holds a relationship expressed by, $$E = E_0 + 2.303(RT/ZF) \log a$$

in which the logarithm of the activity changes in proportion to the potential, and from which a desired ionic activity can be easily calculated from the potential that is measured. In the above formula, R is a gas constant, T is an absolute temperature, Z is a valency, F is a Faraday constant, and $E_0$ is a standard electrode potential of the system. Use of this ion sensor makes it possible to determine the ions over a wide range of concentrations by simply measuring the potential.

The chloride ion sensor chiefly uses a quaternary ammonium salt as an tonically sensitive substance, and study has been conducted extensively in an effort to improve the selectivity (Mikrochimica Acta [Wien], 1984, III, 1–16). Japanese Patent Application No.23151/1989 teaches a sensor featuring excellent selectivity, in which a tetraoctadecylammonium salt is carried as a sensitive substance by a high-molecular support film such as of polyvinyl chloride. In the sensor using an ion sensitive liquid membrane, water is permitted to pass through little due to the use of an ester, an alcohol and a polyvinyl chloride having a high oleophilic property as a main component of a membrane, the water migrates little in the inner solution, and the composition of the inner solution remains stable. There, however, remains a problem in that the slope sensitivity of the electrode loses stability due to the elution of the sensitive substance and of the plasticizer. There have further been known sensors using an ion-exchange membrane in which a quaternary ammonium salt is fixed to a polymer matrix as taught in JP-A-57-40642 and JP-B-2-13262. It is considered that the slope sensitivity of the electrode remains highly stable since the sensitive substance has been fixed and elutes out very little. However, the ion-exchange membrane has been developed in order to remove the salt and, hence, permits ions to easily pass through and, accordingly, permits the water to easily pass through. If the ion-exchange membrane is used as the sensitive film of the ion sensor, there arouses a problem in that water easily migrates in the internal solution whereby the internal solution is depleted and the sensor no longer works. Therefore, there has been reported a method in which a member for suppressing the permeation of water is provided neighboring the ion-exchange membrane as taught in JP-A-2000-28568. As a member for suppressing the permeation of water, there has been used a material that permits water to pass through little but permits ions to pass through easily. Concretely speaking, there have been taught (1) a plasticized polymer membrane in which a quaternary ammonium salt and a plasticizer are dispersed in a polyvinyl chloride, (2) a plasticized polymer membrane in which a quaternary ammonium salt, a crown ether and a plasticizer are dispersed in a polyvinyl chloride, and (3) a polymer membrane in which a polypyrrole film is doped with iodine ions. The polymer membrane is adhered by using an organic solvent to the surface of the ion-exchange membrane on the side opposite to the side that comes in contact with the sample. The sensor incorporating the ion-exchange membrane integrally formed with the water permeation-suppressing member formed by those methods, suppresses a drop in the slope sensitivity even after preserved for three months.

SUMMARY OF THE INVENTION

The present inventors have studied a sensor by using a polyvinyl chloride for the water permeation-suppressing member taught in Examples of the above JP-A-2000-28568, and have discovered that the sensor is capable of suppressing a loss in the sensor weight but has a problem in that the stability of the slope sensitivity is not maintained for extended periods of time.

It is therefore an object of this invention to provide an ion sensor featuring a high stability.

The present invention provides:

(1) An ion sensor comprising a flow path through which a sample flows, an ion-exchange membrane so provided as to come in contact with the sample in said sample flow path, an internal solution (internal gel) provided on one side of said ion-exchange membrane where it does not come in contact with the sample so as to come in contact with the ion-exchange membrane, and an internal electrode provided so as to come in contact with said internal solution, which are arranged in a sealed container, characterized in that the surface of said ion-exchange membrane that does not come in contact with the sample is coated with a reaction-type adhesive.

(2) An ion sensor comprising a flow path through which a sample flows, an ion-exchange membrane so provided as to come in contact with the sample in said sample flow path, an internal solution (internal gel) provided on one side of said ion-exchange membrane where it does not come in contact with the sample so as to come in contact with the ion-exchange membrane, and an internal electrode provided so as to come in contact with said internal solution, which are arranged in a sealed container, characterized in that the surface of said ion-exchange membrane that does not come in contact with the sample is coated with a two-liquid-mixed epoxy resin.

(3) A chloride ion sensor comprising a flow path through which a sample flows, a chloride ion-exchange membrane so provided as to come in contact with the sample in said sample flow path, an internal solution (internal gel) provided on one side of said chloride ion-exchange membrane where it does not come in contact with the sample so as to come in contact with the ion-exchange membrane, and an internal electrode provided so as to come in contact with said internal solution, which are arranged in a sealed container, characterized in that the surface of said chloride ion-exchange membrane that does not come in contact with the sample is coated with a two-liquid-mixed epoxy resin.

(4) A clinical analyzer using an ion sensor of any one of [1] to [3] above.

DESCRIPTION OF THE PREFERRED EMBODIMENTS

Figure 1:
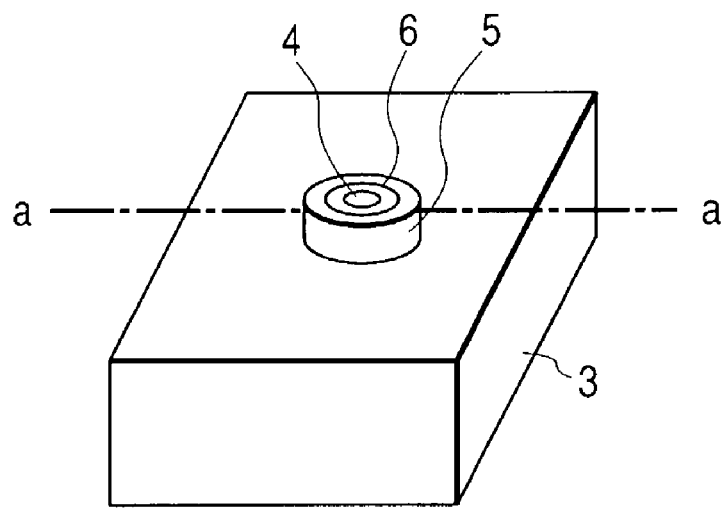
FIG. 1 is a perspective view of a chloride ion sensor fabricated according to the invention.

First, described below are the results of studying the stability of the slope sensitivity of the sensor by using the member for suppressing the permeation of water described in Examples of JP-A-2000-28568 prior to describing the invention. A plasticized polymer membrane in which a quaternary ammonium salt has been dispersed was used as a film material. Thirty percent of a methyltridecylammonium chloride as the quaternary ammonium salt, 50% of a dioctyl sebacate as the plasticizer and 20% of a polyvinyl chloride as the polymer, were weighed in a total amount of 200 mg, and were dissolved in 2 ml of a tetrahydrofuran which is a solvent. The solution was poured and spread into a laboratory dish, and a plasticized polymer membrane was formed as the solvent has evaporated. The film was punched into a suitable shape, and was adhered onto the ion-exchange membrane on the side of the internal solution by using the tetrahydrofuran thereby to form the ion-exchange membrane and the water permeation-suppressing member integrally together. The thus prepared film was incorporated in five chloride ion sensors, and the electrode without the water suppressing member was used as a blank to examine the stability of slope sensitivity in a thermostat maintained at 37° C. Tables 1 and 2 show the preservation periods and changes in the slope sensitivities and in the weight of the sensors. After preserved for three months, the weight of the sensors changed little but the slope sensitivities were lowered.

TABLE 1

Stability of slope sensitivity (unit in mV)

| Preserved (months) | 1 | 2 | 3 | 4 | 5 | 6 |
|---|---|---|---|---|---|---|
| Sensor 1 | −50 | −49 | −46 | −42 | −40 | −40 |
| Sensor 2 | −51 | −50 | −45 | −40 | −37 | −36 |
| Sensor 3 | −50.5 | −50 | −47 | −41 | −36 | −35 |
| Sensor 4 | −51 | −50 | −44 | −40 | −37 | −34 |
| Sensor 5 | −50 | −49 | −44 | −38 | −35 | −35 |
| Blank | −51 | −46 | −41 | −37 | −34 | −34 |

TABLE 2

Change in the weight of the sensors (unit in g)

| Preserved (months) | 1 | 2 | 3 | 4 | 5 | 6 |
|---|---|---|---|---|---|---|
| Sensor 1 | −0.05 | −0.15 | −0.25 | −0.3 | −0.4 | −0.45 |
| Sensor 2 | −0.03 | −0.05 | −0.1 | −0.15 | −0.3 | −0.5 |
| Sensor 3 | −0.1 | −0.1 | −0.15 | −0.2 | −0.3 | −0.6 |
| Sensor 4 | −0.1 | −0.15 | −0.2 | −0.25 | −0.4 | −0.5 |
| Sensor 5 | −0.1 | −0.2 | −0.4 | −0.5 | −0.6 | −0.6 |
| Blank | −0.6 | −1.0 | −1.6 | −2.1 | −2.5 | −2.8 |

It was learned that when the polyvinyl chloride is used as the water permeation-suppressing member, a loss in the weight of the sensor can be suppressed but the stability of the slope sensitivity cannot be maintained for extended periods of time.

When the ion sensor employing the ion-exchange membrane as the ion sensitive membrane is used for extended periods of time, the water in the internal solution provided between the internal electrode and the ion-exchange membrane escapes into the sample flow path through the ion-exchange membrane with the passage of time, whereby the electric conductivity decreases and the sensor performance decreases. In order to decrease the loss of water, the surface of the ion-exchange membrane is coated with a polymer on the side that does not come in contact with the sample but comes in contact with the internal solution. Thus, the permeability of water in the internal solution through the membrane is controlled to realize a high degree of stability. The polymer that are used must intimately adhere onto the ion-exchange membrane and must have pores through which the water permeates. If the water does not permeate at all, the electric conductivity is not exhibited and the sensor function is not obtained. The water which excessively permeates, on the other hand, escapes into the sample flow path, and the sensor loses the stability. If the water permeates, the adhesion decreases between the polymer and the ion-exchange membrane, whereby the electric conductivity decreases as the polymer is partly or entirely peeled off. Therefore, the polymer best suited for the invention is such that the water is allowed to permeate to a suitable degree and maintains a state where the polymer is not peeled off the ion-exchange membrane for extended periods of time.

As a result of fabricating the sensors using various polymer and studying the performance thereof, it was found that the epoxy resin was best suited as a polymer satisfying the above-mentioned conditions. Though the mechanism has not been clarified yet, it is presumed that (1) the epoxy resin adheres well to the ion-exchange membrane in a dry state, (2) when brought into contact with the water, the water infiltrates into the epoxy resin and a suitable degree of electric conductivity is exhibited, and (3) even when the water has infiltrated therein, the epoxy resin stays adhered to the ion-exchange membrane. A small gap was observed between the polyvinyl chloride film and the ion-exchange membrane in all of the sensors that have used the aged polyvinyl chloride as the high-molecular coating material described in the "Problems to be Solved" above. This is presumably due to that the polyvinyl chloride film cannot stay adhered to the ion-exchange membrane for extended periods of time.

A. Coating the Back Surface of the Ion-Exchange Membrane with a Polymer.

About 50 mg of a two-liquid-mixed epoxy resin was applied onto the back surface of the ion-exchange membrane that does not come in contact with the sample, and was tried at 40° C. for 24 hours to form a polymer film thereon.

B. Fabrication of Ion Sensor.

Figure 2:
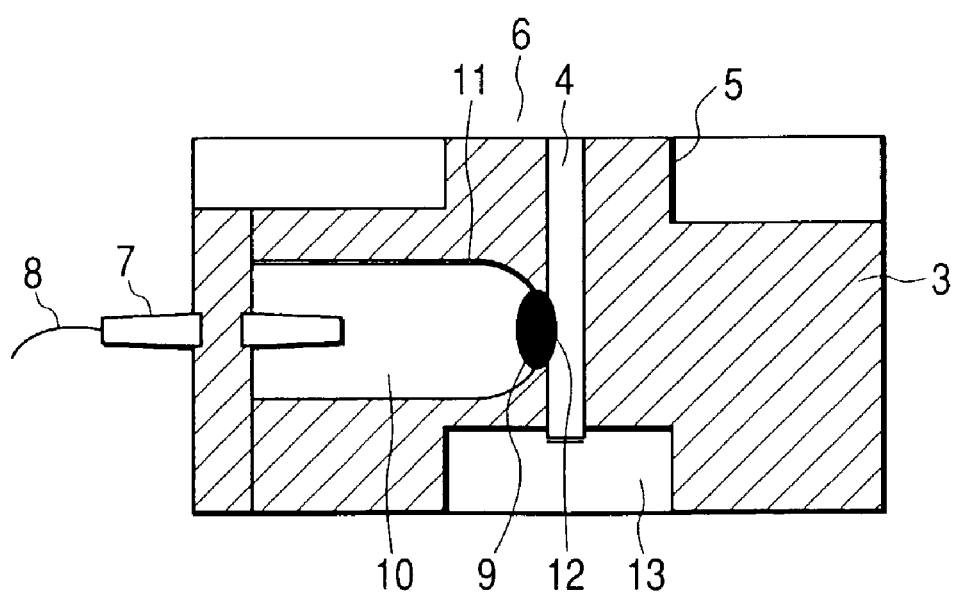
FIG. 2 is a sectional view of the chloride ion sensor fabricated according to the invention.

FIGS. 1 and 2 illustrate an example of fabricating a chloride ion sensor according to the invention. FIG. 1 is a perspective view of a flow cell-type chloride ion sensor fabricated according to the invention. A flow path 4 having a diameter of 1 mm was formed across a pair of surfaces of a flow cell-type sensor body 3 of a rectangular parallelopiped shape made of a polyvinyl chloride, and was used as a sample solution flow path. When the sensors are to be used in a plural number being overlapped one upon the other, a cylindrical protuberance 5 is formed on one surface in which the through hole has been formed for joining the sensors. An O-ring 6 for preventing the leakage of solution is placed on the upper surface of the protuberance 5.

FIG. 2 is a sectional view cut along the line a–a' of FIG. 1. A cavity 10 is formed in a portion of the flow cell-type sensor body 3. An inner curved surface 11 which is curved in one direction in the cavity 10 is intersecting the flow path 4, and a small hole 12 of an elliptic shape is formed in the side surface of the flow path. An ion-exchange membrane 9 is formed along the inner curved surface 11 so as to close the small hole 12 and protruding on the flow path side.

The selectively treated ion-exchange membrane was punched in a round shape by using a cork borer of an inner diameter 4.6φ, adhered to the body of a flow cell-type electrode with THF, and was dried for one hour. About 50 mg of the polymer was applied to the back surface of the film and was, then, dried at 40° C. for 24 hours. The cavity 10 on the side opposite to the flow path has been filled with the internal solution. An internal electrode 7 of silver/silver halide was immersed in the internal solution, and a lead wire 8 for taking out signals was connected at its one end to a metallic portion of the internal electrode 7 and was connected at its other end to an external measuring circuit.

C. Measurement 1 (Initial Performance Test).

Figure 5:
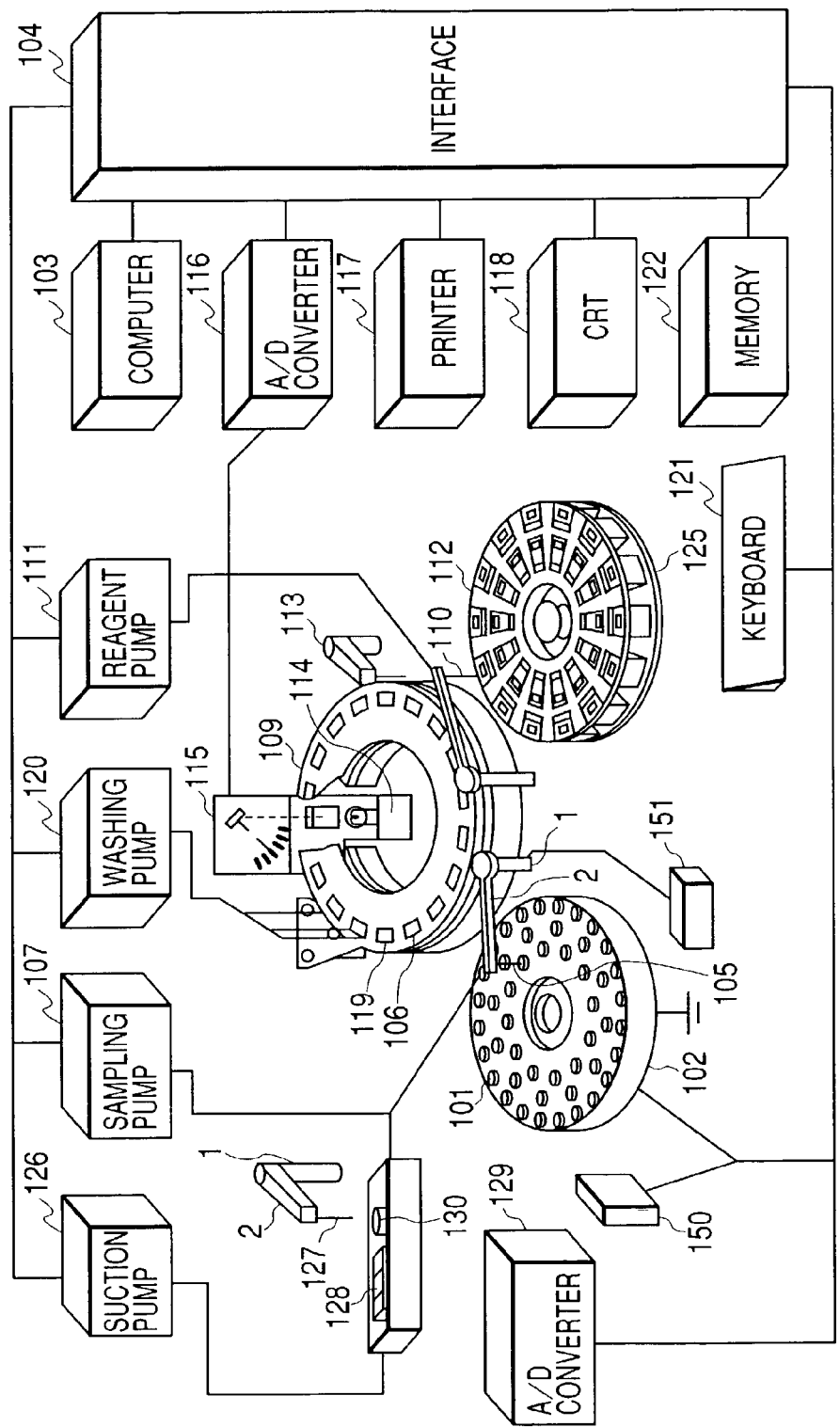
FIG. 5 is a diagram illustrating the constitution of a clinical analyzer to which the invention is applied.

The ion-exchange membranes were treated with various polymer to fabricate flow cell-type electrodes which were, then, evaluated by using a clinical analyzer, Model 7170, manufactured by Hitachi, Ltd. FIG. 5 is a diagram illustrating the constitution of the clinical analyzer. Into a diluting vessel 130 were poured a reagent by using a sampling pump 107 and a sample by using a sampling probe 127. The sample to be measured was fed into an ion sensor 128 by a suction pump 126, and the potential that was generated was processed through an A/D converter 129. The results were as tabulated below.

TABLE 3

| Polymer | Slope sensitivity (mV) |
|---|---|
| Cellulose | −46.5 |
| Acetate | −47 |
| Polyvinyl alcohol | −50 |
| Polyvinyl chloride | −51 |
| Polyacrylonitrile | −46 |
| Polyvinylidene chloride | −45 |
| Polyester | −45.5 |
| Polypropylene | −46 |
| Polyurethane | −49.5 |
| Polyacrylic ester | −49 |

TABLE 3-continued

| Polymer | Slope sensitivity (mV) |
|---|---|
| Polyvinyl acetate | −49.5 |
| Polyamide resin | −48 |
| Polyester resin | −47.5 |
| Phenol resin | −50 |
| Melamine resin | −50 |
| Polyurethane | −50.5 |
| Polyether resin | −50 |
| Epoxy resin | −51 |
| ABS resin | −47.5 |
| ACS resin | −47 |
| SBR | −48 |
| NBR | −46 |
| BR | −45.5 |
| Urethane rubber | −47 |
| Acrylic rubber | −48 |
| Silicone rubber | −47 |

For almost all of the polymer used for the experiment, the electrodes exhibited initial slope sensitivities of not smaller than −45 mV. When the ion-exchange membranes were coated with polymer on the side of the internal solution, it was learned that the polymer were not complete insulators but exhibited electric conductivities. The slope sensitivities differ depending upon the polymer probably due to differences in the electric conductivities of the polymer.

D. Measurement 2 (Load Test).

Figure 3:
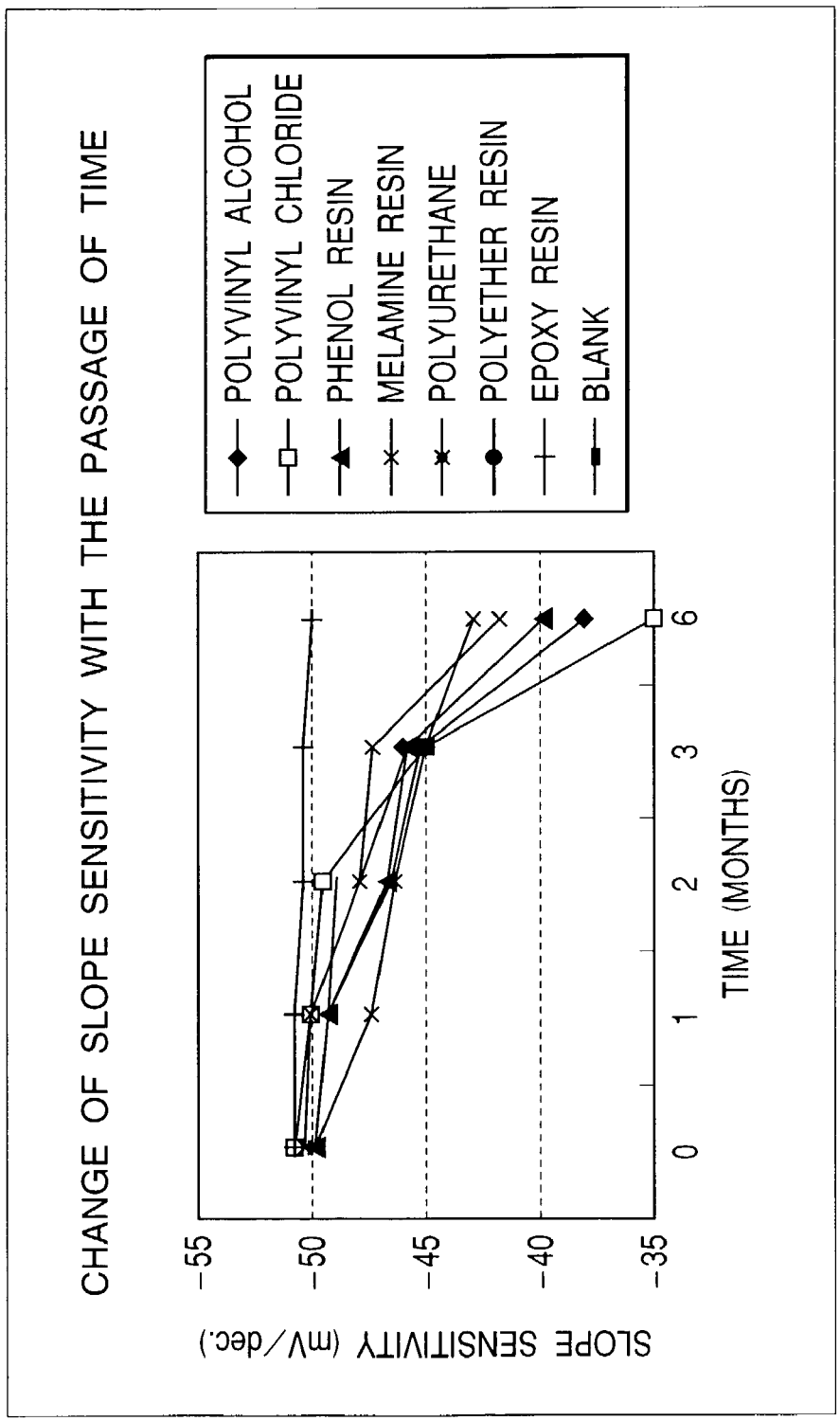
FIG. 3 illustrates the results of changes in the slope sensitivities with the passage of time in the measurement 2 according to the invention.
Figure 4:
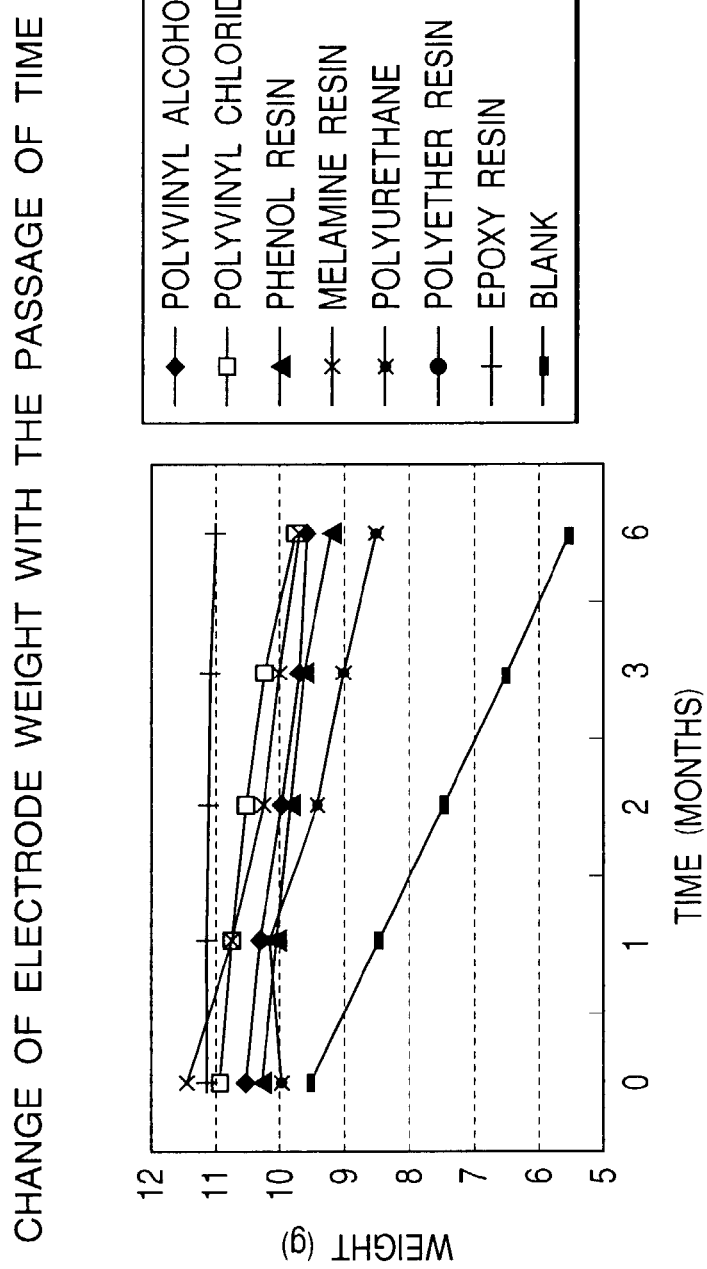
FIG. 4 illustrates the results of changes in the weight of electrodes with the passage of time in the measurement 2 according to the invention.

Highly sensitive electrodes exhibiting initial slope sensitivities of not smaller than −50 mV were examined for their durability relying upon the load test. In order to evaluate the stability, the electrodes were preserved in a thermostat maintained at 60° C., and changes in the slope sensitivity and in the weight of the electrodes with the passage of days were plotted. The results were as shown in FIGS. 3 and 4.

While preserved in the thermostat for about six months, there were observed changes in the slope sensitivities and in the weight of the electrodes. In the case of a blank without coated with the polymer, the weight decreased by about 3 g after three months have passed and no slope sensitivity was exhibited. Among the polymer, only the epoxy resin with which the electrode was applied exhibited favorable results with a small drop in the slope. It was therefore learned that upon treating the back surface of the ion-exchange membrane which is not in contact with the sample with a polymer, it is allowed to control the permeability of water in the internal solution through the film and to realize an improved stability without permitting the polymer to peel off.

Upon treating the back surface of the ion-exchange membrane which is not in contact with the sample with a polymer, it is allowed to control the permeability of water in the internal solution through the film and to realize an improved stability.

What is claimed is:

1. An ion sensor comprising a flow path through which a sample flows, an ion-exchange membrane so provided as to come in contact with the sample in said sample flow path, an internal solution provided on one side of said ion-exchange membrane where it does not come in contact with the sample so as to come in contact with said ion-exchange membrane, and an internal electrode provided so as to come in contact with said internal solution, which are arranged in a sealed container, wherein the surface of said ion-exchange membrane that does not come in contact with the sample is coated with a reaction-type adhesive.

2. An ion sensor comprising a flow path through which a sample flows, an ion-exchange membrane so provided as to come in contact with the sample in said sample flow path, an internal solution provided on one side of said ion-exchange membrane where it does not come in contact with the sample so as to come in contact with said ion-exchange membrane, and an internal electrode provided so as to come in contact with said internal solution, which are arranged in a sealed container, wherein the surface of said ion-exchange membrane that does not come in contact with the sample is coated with a two-liquid-mixed epoxy resin.

3. A chloride ion sensor comprising a flow path through which a sample flows, a chloride ion-exchange membrane so provided as to come in contact with the sample in said sample flow path, an internal solution provided on one side of said chloride ion-exchange membrane where it does not come in contact with the sample so as to come in contact with said ion-exchange membrane, and an internal electrode provided so as to come in contact with said internal solution, which are arranged in a sealed container, wherein the surface of said chloride ion-exchange membrane that does not come in contact with the sample is coated with a two-liquid-mixed epoxy resin.

4. A clinical analyzer using an ion sensor of claim 1.

5. A clinical analyzer using an ion sensor of claim 2.

6. A clinical analyzer using an ion sensor of claim 3.

* * * * *